(12) United States Patent
Huang et al.

(10) Patent No.: US 8,394,934 B2
(45) Date of Patent: Mar. 12, 2013

(54) METHOD AND PROCESS FOR SYNTHESIS OF 2',3'-DIDEHYDRO-2', 3'-DIDEOXYNUCLEOSIDES

(76) Inventors: Zhen Huang, Marietta, GA (US); Jia Sheng, Atlanta, GA (US)

( * ) Notice: Subject to any disclaimer, the term of this patent is extended or adjusted under 35 U.S.C. 154(b) by 12 days.

(21) Appl. No.: 12/933,619

(22) PCT Filed: Mar. 20, 2009

(86) PCT No.: PCT/US2009/037823
§ 371 (c)(1),
(2), (4) Date: Dec. 9, 2010

(87) PCT Pub. No.: WO2009/117668
PCT Pub. Date: Sep. 24, 2009

(65) Prior Publication Data
US 2011/0105743 A1    May 5, 2011

Related U.S. Application Data

(60) Provisional application No. 61/038,439, filed on Mar. 21, 2008.

(51) Int. Cl.
*C07H 1/00* (2006.01)
*C07H 19/00* (2006.01)
*C07H 19/22* (2006.01)
*C07H 19/048* (2006.01)
*C07D 307/02* (2006.01)

(52) U.S. Cl. .................. 536/1.11; 536/27.11; 536/27.14; 536/28.2; 549/507

(58) Field of Classification Search .................. None
See application file for complete search history.

(56) References Cited

U.S. PATENT DOCUMENTS 5,410,033 A * 4/1995 Clive et al. .................. 536/27.14
7,592,446 B2   9/2009 Huang

* cited by examiner

*Primary Examiner* — Lawrence E Crane
(74) *Attorney, Agent, or Firm* — Arnall Golden Gregory LLP; R. Stevan Coursey, Esq.

(57) ABSTRACT

A method is disclosed for synthesizing 2',3'-didehydro-2',3'-dideoxynucleosides (d4Ns) from a nucleophile-mediated elimination, such as a telluride-mediated elimination reaction. After substitution of 2,2'-anhydronucleosides with a nucleophile, such as a telluride monoanion, a telluride intermediate is formed, and its elimination leads to formation of the olefin products (d4Ns). This disclosure describes this telluride-assisted (or nucleophile-assisted) reaction and how to facilitate the substitution and elimination in order to form d4Ns.

12 Claims, No Drawings

METHOD AND PROCESS FOR SYNTHESIS OF 2',3'-DIDEHYDRO-2', 3'-DIDEOXYNUCLEOSIDES

CROSS-REFERENCE TO RELATED APPLICATIONS

This application claims benefit of U.S. Provisional Application No. 61/038,439, filed Mar. 21, 2008. Application No. 61/038,439, filed Mar. 21, 2008, is hereby incorporated herein by reference in its entirety.

STATEMENT OF GOVERNMENT LICENSE RIGHTS

This invention was made with Government support under Grant No. MCB-0517092 awarded by the National Science Foundation. The Government has certain rights in this invention.

FIELD OF THE INVENTION

The disclosure is related to synthetic methods for the production of 2',3'-didehydro-2',3'-dideoxynucleosides (d4Ns).

BACKGROUND OF THE INVENTION

The FDA has approved the use of several 2',3'-dideoxynucleosides (ddNs) and 2',3'-didehydro-2',3'-dideoxynucleosides (d4Ns) in anti-HIV drugs. These compounds are important antiviral compounds, which terminate viral DNA polymerization after their incorporation by reverse transcriptase. Specifically, the FDA has approved the use of 2',3'-dideoxycytidine (ddC); 2',3'-didehydro-3'-deoxythymidine (d4T, Stavudine); 3'-azido-3'-deoxythymidine (AZT); 2',3'-dideoxyinosine (ddI); β-3'-deoxy-3'-thiocytidine (3TC); Abacavir (ABC); and Emtricitabine in anti-HIV therapeutics.

Currently, d4Ns can be synthesized using several popular methods. For example, these methods include the Corey-Winter reaction through cyclic thionocarbonates, the Eastwood olefination through cyclic orthoformates, the Mattocks reaction through bromoacetates, and olefin metathesis via a ring closure reaction. In addition, 2',3'-anhydro-2'-deoxy-uridine and -thymidine can be converted to d4Ns via base-catalyzed elimination. Furthermore, d4Ns may also be synthesized via oxidative elimination of nucleoside α-phenylselenoxides and via substitution of nucleoside dimesylates by selenide and telluride dianions. In some cases, these methods can be expensive, can vary in complexity and ease, and can undesirably increase the cost of disease treatment.

Therefore, there exists a need for new synthetic methods of d4Ns which can provide additional options for preparing d4Ns. There is also a need for additional synthetic methods that have the potential of reducing the costs of disease treatment as well as novel analog/drug discovery.

BRIEF SUMMARY OF THE INVENTION

This disclosure provides new methods for synthesizing d4Ns, which provides additional options for preparing anti-HIV drugs, and which can be relatively cost effective and efficient. It has been demonstrated that selenium functionality can be successfully introduced to the α-2-position by reacting sodium methylselenide (reduced from dimethyl diselenide with NaBH$_4$) with 2,2-anhydronucleosides (Scheme 1). This reaction produces the 2-SeMe-nucleosides. Unlike selenium, introduction of a telluride did not produce the expected 2-Te-nucleosides. Instead, the addition of telluride resulted in the formation of eliminated 2,3- and 1,2-olefin products. By tailoring the SN2 leaving ability of the 3-moieties (such as acetylation), the telluride-mediated elimination may produce the 2,3-olefins (or d4Ns) exclusively.

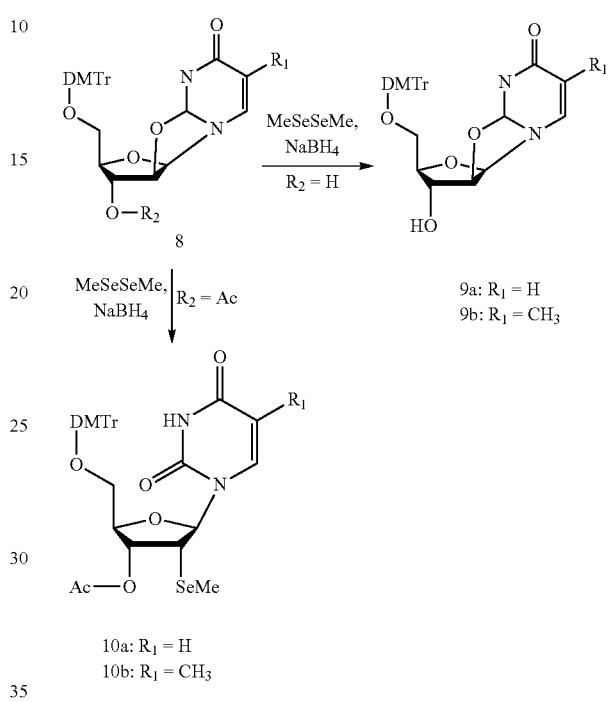

Among other things, this disclosure describes a method of synthesizing 2,3-didehydro-2,3-dideoxynucleosides comprising: providing a 2,2-anhydronucleoside; contacting the 2,2-anhydronucleoside with telluride dianion, or an alkyl or aryl telluride monoanion having from 1 to 24 carbon atoms, to form a product or an intermediate; and contacting the product or the intermediate with an oxidizing agent, a reducing agent, or a nucleophile, if desired or necessary, to facilitate the elimination of a telluride dianion-derived substituent, an alkyl or aryl telluride monoanion-derived substituent, or another leaving group from the product or the intermediate.

In one aspect, the 2,2-anhydronucleoside is protected at the 5 and 3 positions using conventional methodologies. Possible protecting groups include, but are not limited to, the following: diemethoxytrityl (DMTr), trityl (Tr), alkyl (Ak) having from 1 to 24 carbon atoms, aryl (Ar) having up to 14 carbon atoms, benzyl (Bn), acetyl, benzoyl, methylbenzoyl, trifluoromethylbenzoyl, methanesulfonyl (Ms), trifluoromethanesulfonyl (Tf, para-toluenesulfonyl (Ts), chloro (Cl), bromo (Br), iodo (I), trimethylsilyl (TMS), tert-butyldimethylsilyl (TBDMS), and any silyl having from 3 to 24 carbon atoms. In another aspect, the telluride monoanion species can be generated by reduction of an alkyl or aryl ditellurium species. For example, the resulting telluride monoanion species may be a methyl telluride monoanion or a phenyl telluride monoanion. Telluride dianion can be generated from reduction of tellurium by an appropriate reducing agent such as LiAlH$_4$.

The elimination of the alkyl or aryl telluride monoanion derived substituent may occur in situ. In other aspects, the elimination of the alkyl or aryl telluride monoanion derived substituent may be facilitated by the addition of an oxidizing or reducing agent. In one aspect, water and iodine may be used to create the oxidative conditions. Similarly, the oxidizing agent can be selected from air, $O_2$, $NaIO_4$, or $H_2O_2$. In another aspect, sodium borohydride, $LiAlH_4$, $LiBH_4$, $B_2H_6$, NaHS, $NaHSO_3$, Zn, Fe, Al, $H_2$, or other similar reducing agents may be used as the reducing agent.

In certain aspects of this disclosure, adjusting the functionality at the 3 position of the 2,2-anhydronucleosides enables control over the olefin product formed. The leaving ability of the 3 moiety may guide the elimination of the telluride dianion-derived, or the alkyl or aryl telluride monoanion derived substituent.

DETAILED DESCRIPTION OF THE INVENTION

This disclosure describes a method of synthesizing 2,3-didehydro-2,3-dideoxynucleosides comprising providing a 2,2-anhydronucleoside, reacting the 2,2-anhydronucleoside with telluride dianion, an alkyl or aryl telluride monoanion having from 1 to 24 carbon atoms, or another nucleophile, and facilitating, if desired or if necessary, elimination of telluride dianion, the alkyl or aryl telluride monoanion derived substituent, or the nucleophile-derived substituent with the addition of an oxidizing agent, a reducing agent or a nucleophile.

In one aspect, the 2,2-anhydronucleoside is protected at the 5 and 3 position using conventional methodologies. Possible protecting groups include, but are not limited to, the following: diemethoxytrityl (DMTr), trityl (Tr), alkyl (Ak) having from 1 to 24 carbon atoms, aryl (Ar) having up to 14 carbon atoms, benzyl (Bn), acetyl, benzoyl, methylbenzoyl, trifluoromethylbenzoyl, methanesulfonyl (Ms), trifluoromethanesulfonyl (Tf, para-toluenesulfonyl (Ts), chloro (Cl), bromo (Br), iodo (I), trimethylsilyl (TMS), tert-butyldimethylsilyl (TBDMS), and any silyl having from 3 to 24 carbon atoms. In other aspects, the 2,2-anhydronucleoside comprises the following structure:

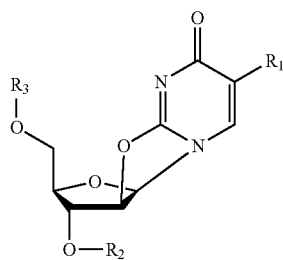

(I)

wherein $R_1$ is a hydrogen or an alkyl having from 1 to 10 carbon atoms;

wherein $R_2$ is a hydrogen, benzoyl, dimethoxytrityl (DMTr), trityl (Tr), alkyl (Ak) having from 1 to 24 carbon atoms, aryl (Ar) having up to 14 carbon atoms, benzyl (Bn), acetyl, benzoyl, methylbenzoyl, trifluoromethylbenzoyl, methanesulfonyl (Ms), trifluoromethanesulfonyl (Tf), para-toluenesulfonyl (Ts), chloro (Cl), bromo (Br), iodo (I), trimethylsilyl (TMS), tert-butyldimethylsilyl (TBDMS), a silyl having from 3 to 24 carbon atoms, or an acyl having from 1 to 12 carbon atoms; and wherein $R_3$ is a hydrogen, benzoyl, dimethoxytrityl, trityl (Tr), alkyl (Ak) having from 1 to 12 carbon atoms, aryl (Ar) having up to 14 carbon atoms, benzyl (Bn), benzoyl, methylbenzoyl, trifluoromethylbenzoyl, trimethylsilyl (TMS), tert-butyldimethylsilyl (TBDMS), acetyl, an acyl having from 1 to 12 carbon atoms, a silyl having from 3 to 24 carbon atoms, an acyl having from 1 to 12 carbon atoms, or any other protecting group.

The alkyl or aryl telluride monoanion having from 1 to 24 carbons may be generated from a ditellurium species with the formula $R_1Te$—$TeR_2$ wherein $R_1$ and $R_2$ are selected independently from an alkyl or an aryl group having from 1 to 24 carbon atoms. The ditellurium species may be reduced by any acceptable reducing agent to form the alkyl or aryl telluride monoanion species. In one aspect, the ditellurium species may be reduced by sodium borohydride. The resulting telluride monoanion species may be a methyl telluride monoanion or a phenyl telluride monoanion. In another aspect, the ditelluride reagent can be reduced by $LiAlH_4$, $LiBH_4$, $B_2H_6$, NaHS, $NaHSO_3$, Zn, Fe, Al, or $H_2$.

In another aspect, nucleophiles other than the telluride dianion, or an alkyl or aryl telluride monoanion can be used in this process. For example, suitable nucleophiles include, but are not limited to, hydride ion, sulfide, 2-mercaptoethanol, dithiothreitol (DTT), hydroxide, ammonia, cyanide, and another appropriate nucleophiles.

The addition of the alkyl or aryl telluride monoanion species may occur at the alpha-2 position of the 2,2-anhydronucleoside. In one aspect, the elimination of the alkyl or aryl telluride monoanion derived substituent may occur in situ. In other aspects, the elimination of the alkyl or aryl telluride monoanion-derived substituent may be facilitated by the addition of an oxidizing agent, a reducing agent, or a nucleophile. Whether the elimination occurs in situ or requires facilitation with an oxidizing or reducing agent may depend on the characteristics of the alkyl or aryl ditelluride monoanion species. In particular aspects, altering the number of carbon atoms in the alkyl or aryl telluride monoanion species may increase or decrease the speed and/or ease of elimination.

In one aspect, iodine and water may be used to create oxidative conditions to facilitate the elimination of the alkyl or aryl telluride monoanion derived species when the elimination does not occur in situ. In another aspect, sodium borohydride may be used as a reducing agent to facilitate the elimination of the alkyl or aryl telluride monoanion derived species when the elimination does not occur in situ.

In other aspects, adjusting the functionality at the 3 position of the 2,2-anhydronucleoside may enable control over which olefin product may be formed. In one aspect, $R_2$ in structure (I) above is hydrogen and methyl telluride monoanion is the reactive species. In this aspect, elimination may occur across the 1-2 bond to form 13 (Scheme 2) instead of a 2,3-didehydro-2,3-dideoxynucleoside. In other aspects, if $R_2$ is not hydrogen, a 2,3-didehydro-2,3-dideoxynucleoside may form upon the elimination of the telluride monoanion derived species. The leaving group ability at the 3 position may play a significant role in determining the regioselectivity of the elimination.

In other aspects, any electron withdrawing substituent at the $R_2$ position in structure (I) may facilitate elimination of the alkyl or aryl telluride monoanion derived species to produce a 2,3-didehydro-2,3-dideoxynucleoside.

In one particular aspect, the 2,2-anhydronuclesode 8, as seen in Scheme 2, may be prepared via the well-established 2,2-anhydronucleoside synthesis from the readily available ribonucleosides, followed by protection of the 5 and 3 hydroxyl groups using conventional methodologies.

The telluride-mediated elimination described in this disclosure, may undergo a two-step mechanism: substitution (or addition) and elimination. One aspect of this hypothesis is illustrated in Scheme 2. According to this hypothesis, dimethyl ditelluride is first reduced to methyltelluride monoanion. Via a SN2 reaction, this strong telluride nucleophile may attack the α-2-position of 2,2-anhydronucleosides by substituting the 2-oxide as the intramolecular leaving group, which may lead to formation of a substitution (or addition) intermediate (11). This intermediate may undergo an elimination to give 2,3-olefin (12, d4N) and 1,2-olefin (13). The 2,3-olefin (12) would itself appear to have utility as a precursor or as an anti-HIV drug, either alone or in combination with other anti-HIV drugs.

When dimethyl ditelluride ($Me_2Te_2$) is used as the reagent, the expected intermediate 11 may not be isolated. The instability of the intermediate may be caused by the highly-reactive alkyl telluride. Thus, it may be possible that a less-reactive aryl telluride may facilitate isolation of the intermediate.

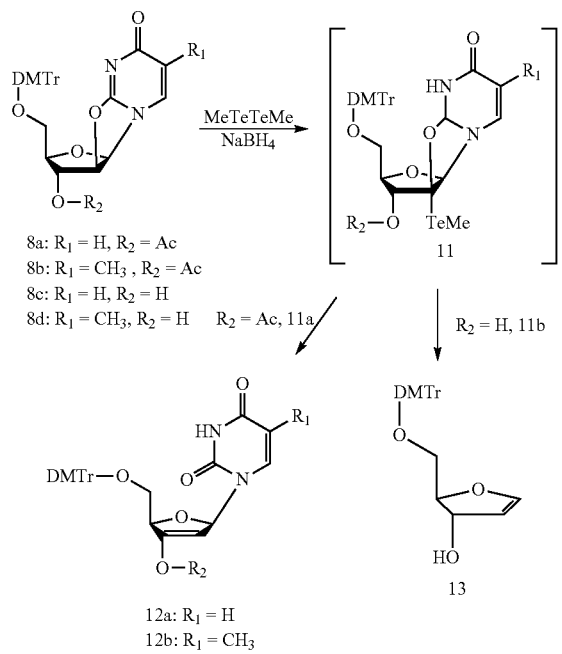

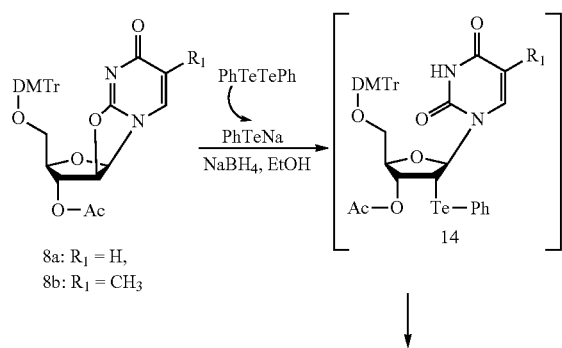

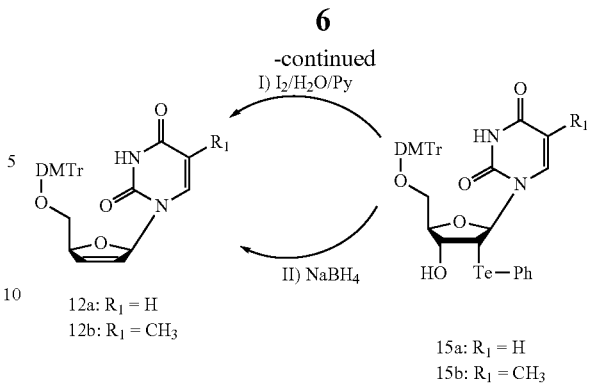

In one aspect, diphenyl telluride monoanion may be used in the process described in this disclosure. When diphenyl ditelluride is used as the reagent, the telluride intermediate may be successfully isolated. Due to the 3-deacetylation under basic conditions in ethanol, however, intermediate 15 with the 2-Ph-Te functionality may be isolated instead of the 3-Ac intermediate (14, Scheme 3). Similar to oxidative elimination of the nucleoside phenylselenides, phenyltelluride 15 may also undergo oxidative elimination when treated with iodine/water (Scheme 4), or using oxidizing agents such as air, $O_2$, $NaIO_4$, or $H_2O_2$. Furthermore, the cis-2,3-elimination of 15 may also occur when it is treated with $NaBH_4$, which may explain the formation of a significant amount of 12 formed during the synthesis of phenyltelluride nucleoside 15. Under the oxidative condition, this cis-elimination is probably caused by convenient transfer of the 3-OH to the tellurium functionality in the same face. Under the $NaBH_4$ reduction, the telluride is probably reduced first by hydride, thereby generating a carbanion at the 2-position and followed by elimination via an E1cb mechanism.

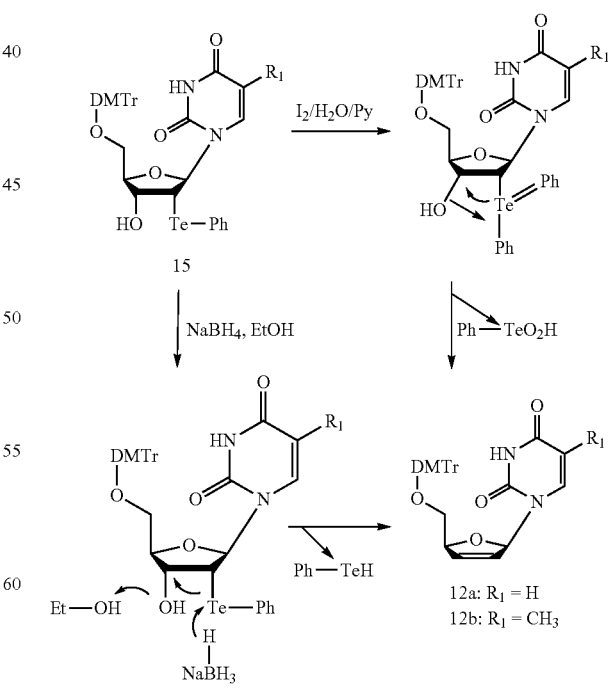

As previously stated, one aspect of this disclosure involves the use of methyl telluride monoanion (Scheme 5). The methyl telluride anion may be generated from a dimethylditellurium species. Sodium borohydride may be added to the $Me_2Te_2$ species to generate the methyl telluride monoanion. Some of the advantages of using $Me_2Te_2$ include, but are not limited to, the following: (i) the substitution-elimination reaction is fast, and (ii) it may lend control over the exclusive formation of the 2,3-elimination products (d4Ns) without isolation of the telluride intermediate. In addition, by placing acyl groups on the 3-positions of 8 and 17, 12 and 18 (5-protected d4Ns) may be exclusively formed with reaction yields up to 90%, when $Me_2Te_2$ (0.1 eq) is used (Table 1). Lower amounts of $Me_2Te_2$ may not work as well, presumably due to the consumption of MeTeH by minor side-reactions. The telluride nucleophile may work as a catalyst in this elimination reaction. The telluride nucleophile (R—TeNa or R—TeH) may first be generated by $NaBH_4$ reduction of the ditelluride reagent (RTe—TeR) and regenerated by reductive elimination of the telluride intermediate, such as 15. In other aspects, any acceptable reducing agent may be used to generate the reactive alkyl or aryl telluride monoanion species. Since the methyl-telluro group at the 2-position is more reactive than the phenyl-telluro group and offers high yield, it may be better to use MeTe—TeMe for the elimination reaction, where longer reaction time and the Te-intermediate isolation are not necessary.

In other aspects, a bulky DMTr group may be added to the 3-position of 17c (Scheme 5). Due to the steric hindrance of this protecting group, which may inhibit the attack of the bulky telluride at the 2-α-position, no elimination reaction was observed (Table 1). Furthermore, when the 3-OH of 8c was not activated, 13 was formed via 1,2-elimination (Scheme 2). Note that in 13, DMTr can be replaced by trityl (Tr), alkyl (Ak) having from 1 to 12 carbon atoms, aryl (Ar) having up to 14 carbon atoms, benzyl (Bn), benzoyl, methylbenzoyl, trifluoromethylbenzoyl, trimethylsilyl (TMS), tert-butyldimethylsilyl (TBDMS), acetyl, an acyl having from 1 to 12 carbon atoms, or a silyl having from 3 to 24 carbon atoms. Moreover, when both the 3- and 5-positions of 17 were protected with the same acyl group for convenient synthesis (e.g., Ac- or Bz-), satisfactory elimination yields of d4Ns may be obtained. These various aspects reveal that a moderate leaving group at the 3-positions may provide sufficient regioselectivity for the d4N synthesis, and that the 5-position may not be involved in the Te-assisted substitution-elimination reaction.

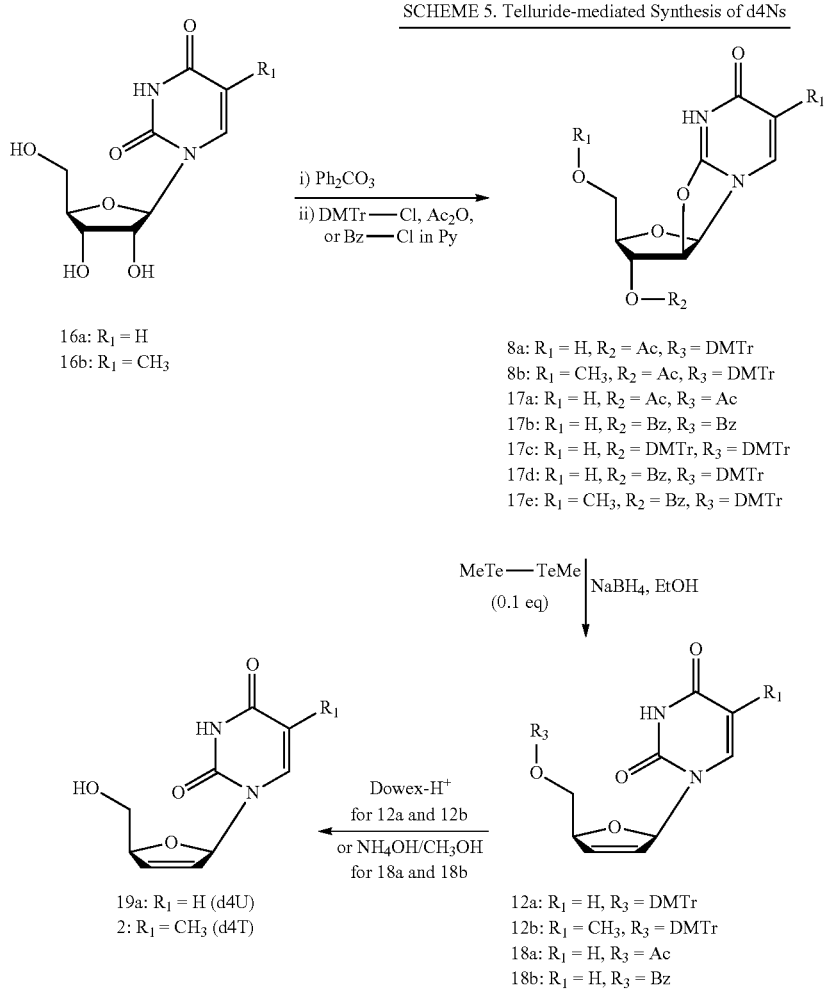

SCHEME 5. Telluride-mediated Synthesis of d4Ns

TABLE 1

Synthesis of d4Ns via Te-assisted elimination (for Scheme 5):

| Substrates | $R_1$ | $R_2$ | $R_3$ | Products | Yield (%) |
|---|---|---|---|---|---|
| 8a | H | Ac | DMTr | 12a | 90 |
| 8b | $CH_3$ | Ac | DMTr | 12b | 85 |
| 17a | H | Ac | Ac | 18a | 80 |
| 17b | H | Bz | Bz | 18b | 69 |
| 17c | H | DMTr | DMTr | None | — |

*DMTr: dimethoxytrityl.

Unless indicated otherwise, when a range of any type is disclosed or claimed, for example a range of distance or length, percent or frequency, number of discharge cycles, or time periods, it is intended to disclose or claim individually each possible number that such a range could reasonably encompass, including any sub-ranges encompassed therein. For example, when the Applicants disclose or claim an adjustment in time from about 0.1 to about 2 seconds, Applicants' intent is to disclose or claim individually every possible number that such a range could encompass, consistent with the disclosure herein. Thus, by the disclosure that a time adjustment can range from about 0.1 to about 2 seconds, Applicants intent is to recite that the time adjustment can be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0 seconds, including any ranges, sub-ranges, or combinations thereof between any disclosed times. Accordingly, Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants are unaware of at the time of the filing of the application.

All publications and patents mentioned in the disclosure are incorporated herein by reference in their entireties, for the purpose of describing and disclosing, for example, the constructs and methodologies that are described in the publications, which might be used in connection with the presently described process and apparatus. The publications discussed above and throughout the text are provided solely for their disclosure prior to the filing date of the present application. Nothing herein is to be construed as an admission that the inventors are not entitled to antedate such disclosure by virtue of prior invention. Should the usage or terminology used in any reference that is incorporated by reference conflict with the usage or terminology used in this disclosure, the usage and terminology of this disclosure controls. The Abstract of the disclosure is provided herewith to satisfy the requirements of 37 C.F.R. §1.72 and the purpose stated in 37 C.F.R. §1.72 (b) "to enable the United States Patent and Trademark Office and the public generally to determine quickly from a cursory inspection the nature and gist of the technical disclosure." The Abstract is not intended to be used to construe the scope of the appended claims or to limit the scope of the subject matter disclosed herein. Any use of the past tense to describe an example otherwise indicated as constructive or prophetic is not intended to reflect that the constructive or prophetic example has actually been carried out.

EXAMPLES

Example 1

Synthesis of 5-Methyluridine or ribothymidine 5-methyluridine was synthesized from thymine and the acylated ribose via glycosidation by following minor modifications of common procedures found in the literature. Thymine (3.80 g, 30.2 mmol) and 1-O-acetyl-2,3,5-tri-O-benzoylribose (12.7 g, 25.4 mmol) were suspended in anhydrous acetonitrile (350 mL), and trimethylsilyl chloride (3.2 mL, 25.9 mmol) and hexamethyldisilazane (5.3 mL, 25.4 mmol) were added. The suspension was stirred until a clear solution was obtained, then tin tetrachloride (2.97 mL, 25.4 mmol) were added into the reaction solution. The resulting suspension was heated to reflux for 1.5 h. The solution was concentrated under reduced pressure to a small volume (approximately 20 mL), and methylene chloride (100 mL) was then added to it. The organic layer was washed with water (20 mL), saturated sodium bicarbonate (2×20 mL), and brine (20 mL), dried over $MgSO_4$ and concentrated to give 2',3',5'-tri-O-benzoyl-5-methyluridine (crude intermediate) as a white solid (14.36 g). Small amount for NMR analysis was purified by TLC plate. $^1H$ NMR ($CDCl_3$, identical to literature)[7c,12a] δ: 1.61 (s, 3H), 4.72-4.78 (m, 1H), 4.68 and 4.92 (2× dd, $J_1$=2.4 Hz, $J_2$=12 Hz, 2H), 5.78 (t, J=6.0 Hz, 1H), 4.92-4.97 (m, 1H), 6.43 (d, J=6.2 Hz, 1H), 7.18-8.14 (m, 16H). This white solid (14.30 g), without further purification, was dissolved in methanol (350 mL). Sodium methoxide (8.16 g, 151.2 mmol) was then added, and the reaction mixture was stirred at room temperature for overnight. The solution was neutralized with Dowex 50×8-4200 ion-exchange resin (approximately 5 g, monitored by wet pH paper), filtered and concentrated to dryness. The residue was dissolved in water (100 mL), washed with ethyl ether (2×150 mL), and lyophilized. The dry crude product was recrystallized from ethanol to give compound 16b as a white solid (5.76 g, 88% in two steps). $^1H$ NMR ($D_2O$, identical to literature)[7c,12a] δ: 1.78 (s, 3H), 3.72 and 3.83 (2× dd, $J_1$=4.0 Hz, $J_2$=12.8 Hz, 2H), 4.02 (m, 1H), 4.15 (t, J=2.6 Hz, 1H), 4.25 (t, J=2.5 Hz, 1H), 5.82 (d, J=6.0 Hz, 1H), 7.60 (s, 1H).

Example 2

Synthesis of protected 2,2'-anhydronucleosides

This example describes a possible synthetic route for 2,2'-Anhydro-1-[2'-deoxy-3'-acetyl-5'-O-(4,4-dimethoxytrityl)-β-D-arabinofuranosyl]-uracil (8a) or -5-methyluracil (8b). 2,2'-Anhydro-uridine and 2,2'-anhydro-5-methyuridine were first synthesized by following slight modifications of procedures found in the literature. Diphenylcarbonate (7.0 g, 33 mmol) and sodium bicarbonate (0.16 g, 1.8 mmol) were added to the suspension of uridine or 5-methyluridine (22 mmol) in DMF (25 mL). The mixture was heated in an oil bath (100° C.), and the formed carbon dioxide was allowed to escape. 2,2'-anhydrouridine or thymidine product precipitated as a white or tan solid. The reaction was monitored on TLC (15% MeOH in methylene chloride). When the reaction completed in 1.5 hours, the reaction mixture was cooled to room temperature, allowing more precipitation. The precipitate was filtered and washed with cold methanol (10 mL). The yields of both products were about 83-85%. 2,2'-anhydrouridine $^1H$ NMR (DMSO-$d_6$, identical to literature)[3a, 12g] δ: 3.09-3.21 (m, 2H), 3.95-4.11 (m, 1H), 4.25-4.41 (m, 1H), 4.91 (m, 1H), 5.10 (d, J=6.5 Hz, 1H), 5.81 (m, 1H), 5.96 (d, J=7.5 Hz, 1H), 6.22 (d, J=5.7 Hz, 1H), 7.78 (d, J=7.5 Hz, 1H). 2,2'-anhydro-5-methyluridine $^1$H NMR (DMSO-d$_6$, identical to literature)$^{12a,13}$ δ: 1.79 (s, 3H), 3.12-3.25 (m, 2H), 4.05-4.11 (m, 1H), 4.35-4.41 (m, 1H), 5.19 (d, J=5.6 Hz, 1H), 6.29 (d, J=6.2 Hz, 1H), 7.76 (s, 1H).

Then, to a suspension of 2,2'-anhydrouridine or 2,2'-anhydrothymidine (2.85 g or 3.02 g, 12.6 mmol) in dry pyridine (25 mL) was added dimethoxytritylchloride (DMT-Cl, 2.36 g, 6.95 mmol) and the mixture was stirred at room temperature. One hour later, additional DMT-Cl (2.36 g, 6.95 mmol) was added, and the mixture was stirred for another hour (the 5' and 3' di-tritylated products can be isolated as 8c or 8d). Acetic anhydride (1.89 mL, 20 mmol) was then added and the mixture was stirred for 20 minutes at room temperature. The reaction was quenched by the addition of methanol (4 mL), and the solvents were removed under reduced pressure. The residue was dissolved in CH$_2$Cl$_2$ (40 mL) and the suspension was washed with sodium bicarbonate (sat., 2×15 mL) and sat. brine (2×15 mL). The organic layer was dried over MgSO$_4$ (s), concentrated under reduced pressure, and the resulting residue was subjected to silica gel chromatography (0-5% MeOH in CH$_2$Cl$_2$) which gave pure 8a (5.8 g, 87% yield) and 8b (5.9 g, 85% yield) as white solids.

8a: $^1$H NMR (CDCl$_3$) δ: 2.14 (s, 3H), 2.99-3.06 (m, 2H), 3.81 (s, 6H), 4.45 (m, 1H), 5.30-5.32 (m, 1H), 5.40 (m, 1H), 5.86 (d, J=7.6 Hz, 1H), 6.27 (d, J=5.6 Hz, 1H), 6.80-6.83 (m, 4H), 7.21-7.35 (m, 10H); $^{13}$C NMR (CDCl$_3$) δ: 20.7, 55.3, 62.6, 77.0, 85.8, 86.3, 86.6, 90.4, 110.2, 113.3, 127.1, 128.0, 129.8, 135.2, 144.1, 158.6, 134.5, 159.1, 169.4, 171.2; ESI-TOF: m/z calcd for C$_{32}$H$_{31}$N$_2$O$_7$ (M+H)$^+$ 571.2080, found 571.2080; melting point: 126.1-127.2° C.

8b: $^1$H NMR (CDCl$_3$) δ: 1.86 (s, 3H), 2.23 (s, 3H), 2.94-3.04 (m, 2H), 3.80 (s, 6H), 4.42-4.45 (m, 1H), 5.27-5.28 (m, 1H), 5.38 (m, 1H), 6.22 (d, J=5.6 Hz, 1H), 6.76-6.81 (m, 4H), 7.12-7.35 (m, 10H); $^{13}$C NMR (CDCl$_3$) δ: 14.1, 20.7, 55.2, 62.8, 77.1, 85.8, 86.0, 86.6, 90.3, 119.0, 113.2, 127.9, 128.2, 129.8, 135.1, 144.1, 157.1, 130.0, 158.7, 169.6, 171.8; ESI-TOF: m/z calcd for C$_{33}$H$_{33}$N$_2$O$_7$ (M+H)$^+$ 585.2237, found 585.2255; 130.5-131.3° C.

Example 3

Synthesis of protected 2,2'-anhydronucleosides

The following example describes a possible synthetic route for 2,2'-Anhydro-1-(2'-deoxy-3',5'-di-O-acety-β-D-arabinofuranosyl)-uracil (17a), 2,2'-anhydro-1-(2'-deoxy-3',5'-di-O-benzoyl-β-D-arabinofuranosyl)-uracil (17b), and 2,2'-anhydro-1-[2'-deoxy-3',5'-di-(4,4-dimethoxytrityl)-β-D-arabinofuranosyl]-uracil (17c). To the pyridine suspension (10 mL) of 2,2'-anhydrouridine (0.62 g, 2.75 mmol) at room temperature, was added acetic anhydride (for 17a, 0.8 mL, 8.25 mmol), benzoyl chloride (for 17b, 0.95 mL, 8.25 mmol) or the pyridine solution of dimethoxytrityl chloride (for 17c, 1.86 g, 5.5 mmol). The reactions were stirred overnight before quenching with methanol (5 mL) and water (5 mL). The solvents were evaporated under reduced pressure and the residues of 17a, 17b or 17c was dissolved in dichloromethane, washed with saturated sodium dicarbonate, brine and water. The organic layers were combined, dried over MgSO$_4$ (s), and evaporated under reduced pressure. The residue was purified by silica gel column chromatography (gradient, 0-3% of methanol in CH$_2$Cl$_2$). The yields were generally high (88-95%) for the synthesis of 17a-c.

17a: $^1$H NMR (CDCl$_3$, identical to literature)$^{14}$ δ: 2.03 (s, 3H), 2.19 (s, 3H), 4.03-4.07 (dd, 1H, J$_1$=3.6 Hz, J$_2$=12.4 Hz), 4.33-4.37 (dd, 1H, J$_1$=3.6 Hz, J$_2$=12.4 Hz), 4.52-4.54 (m, 1H), 5.41-5.42 (m, 1H), 5.44-5.45 (m, 1H), 6.09 (d, J=7.2 Hz, 1H), 6.30 (d, J=6.4 Hz, 1H), 7.37 (d, J=7.2 Hz, 1H); ESI-TOF: m/z calcd for C$_{13}$H$_{15}$N$_2$O$_7$ (M+H)$^+$ 311.0879, found 311.0883.

17b: $^1$H NMR (DMSO-d$_6$, identical to literature)$^{15}$ δ: 4.34-4.39 (m, 2H), 4.89 (m, 1H), 5.72 (m, 1H), 5.75-5.78 (m, 1H), 5.90 (d, 1H, J=7.2 Hz), 6.49 (d, 1H), J=5.6 Hz), 7.49-8.07 (m, 11H); ESI-TOF: m/z calcd for C$_{23}$H$_{19}$N$_2$O$_7$ (M+H)$^+$ 435.1192, found 435.1177.

17c: $^1$H NMR (CDCl$_3$, identical to literature)$^{16}$ δ: 2.79-2.92 (m, 2H), 3.74 (s, 3H), 3.78 (s, 3H), 3.84 (s, 12H), 3.94-3.96 (m, 1H), 4.32 (m, 1H), 4.77-4.81 (m, 1H), 5.90 (d, J=7.2 Hz, 1H), 5.95 (d, J=5.6 Hz, 1H), 6.78-6.85 (m, 8H), 7.13-7.42 (m, 19H); ESI-TOF: m/z calcd for C$_{51}$H$_{47}$N$_2$O$_9$ (M+H)$^+$ 831.3282, found 831.3277.

Example 4

Elmination of the Telluride Species Across the 1'-2' Bond

This example describes a possible synthetic route for (R)-5-(4,4'-dimethoxytrityloxymethyl)-2,3-dihydrofuran-4-ol (13). To a stirred suspension of NaBH$_4$ (12 mg) in anhydrous THF (5 mL), under argon, dimethyl ditelluride (50 μL, 0.3 mmol) was added, followed by several drops of dry ethanol until bubble formed. The suspension was heated to 50° C., then the THF solution of starting material 8c (0.32 g, 0.6 mmol) was added dropwise. The mixture was heated for three hours at this temperature under argon. The solvent was evaporated under reduced pressure and the residue was then dissolved in CH$_2$Cl$_2$ (20 mL). The solution was washed with water (3×20 mL). The CH$_2$Cl$_2$ layer was dried over MgSO$_4$ (s), evaporated under reduced pressure, and the residue was purified by silica gel column chromatography with pure CH$_2$Cl$_2$ to give compound 13 as white solid (230 mg, 92% yield).

13: $^1$H NMR (CDCl$_3$) δ: 3.18-3.22 (m, 2H), 3.81 (s, 6H), 4.44-4.49 (m, 1H), 4.79-4.81 (m, 1H), 5.20-5.21 (m, 1H), 6.62-6.63 (m, 1H), 6.84-6.86 (m, 4H), 7.23-7.46 (m, 9H,), 7.85 (d, J=7.6 Hz, 1H); $^{13}$C NMR (CDCl$_3$) δ: 55.2, 63.7, 76.2, 86.0, 88.3, 103.3, 113.1, 126.8, 127.8, 128.1, 130.1, 136.0, 144.8, 150.3, 158.5; ESI-TOF: m/z calcd for C$_{26}$H$_{25}$O$_5$ (M−H)$^−$ 417.1702, found 417.1708; melting point: 142.4-143.7° C.

Example 5

Isolation of the 2'-phenyl-telluride Substituted Intermediate

5'-O-(4,4'-dimethoxytrityl)-2'-phenyltelluro-2'-deoxy-uridine (15a) or -thymidine (15b) were isolated after the addition of phenyl telluride monoanion to a 2,-2'anhydronucleoside. To a stirred suspension of NaBH$_4$ (6.2 mg) in anhydrous THF (5 mL), under argon at 0° C., the THF solution of diphenylditelluride (0.2 g, 0.5 mmol in 5 mL) was added, followed by several drops of dry ethanol until bubble formed and the solution turned colorless. To this solution the starting material 8a (0.285 g, 0.5 mmol, dissolved in 5 mL of THF) was added and the reaction was slowly warmed up to room temperature and kept running for three hours at 50° C., which monitored by TLC. The solvent was then evaporated under reduced pressure. The residue was dissolved in CH$_2$Cl$_2$ (20 mL) and washed with water (3×20 mL). The CH$_2$Cl$_2$ solution was dried over MgSO$_4$ (s), and evaporated under reduced pressure. The crude product was purified by silica gel column chromatography (gradient, 0-3% methanol in $CH_2Cl_2$) to give compound 15a as slight yellow solid (163 mg, 42% yield). 15b was synthesized analogously to 15a.

15a: $^1$H NMR (CDCl$_3$) δ: 3.45-3.46 (m, 2H), 3.82 (s, 6H), 3.92-3.95 (m, 1H), 4.24 (m, 1H), 4.54-4.57 (m, 1H), 5.12 (d, J=8 Hz, 1H), 6.63 (d, J=9.2 Hz, 1H), 6.81-6.86 (m, 4H), 7.19-7.37 (m, 12H), 7.45 (d, J=8 Hz, 1H), 7.82 (m, 2H); $^{13}$C NMR (CDCl$_3$) δ: 36.9, 55.3, 63.9, 75.1, 85.5, 87.2, 91.6, 102.5, 109.6, 113.3, 127.2, 127.8, 128.0, 128.1, 128.7, 129.5, 130.1, 135.2, 140.2, 144.2, 150.2, 158.7, 162.7; ESI-TOF: m/z calcd for $C_{36}H_{34}N_2O_7TeNa$ (M+Na)$^+$ 759.1326, found 759.1316; melting point: 135.2-136.3° C.

15b: $^1$H NMR (CDCl$_3$) δ: 1.21 (s, 3H), 2.71-2.83 (m, 1H), 3.36 and 3.51 (2×d, J=10 and 10 Hz, 2H), 3.81 (s, 6H), 3.95-4.06 (m, 1H), 4.21-4.27 (m, 1H), 4.54-4.62 (m, 1H), 6.70 (d, J=10 Hz, 1H), 6.81-6.86 (m, 4H), 7.19-7.41 (m, 12H), 7.84 (m, 2H), 8.18 (s, 1H); $^{13}$C NMR (CDCl$_3$) δ: 11.47, 36.8, 55.3, 63.9, 75.4, 85.2, 87.2, 91.0, 109.5, 111.3, 113.3, 127.2, 128.0, 128.1, 128.6, 129.5, 129.6, 130.1, 135.0, 135.1, 140.3, 144.2, 150.4, 158.8, 163.1; ESI-TOF: m/z calcd for $C_{37}H_{36}N_2O_7TeNa$ (M+Na)$^+$: 773.1477, found 773.1475; melting point: 138.3-140.0° C.

Example 6

Synthesis of 2',3'-didehydro-2',3'-dideoxynucleosides

This example describes the synthesis of 5'-O-(4,4-dimethoxytrityl)-2',3'-didehydro-2',3'-dideoxyuridine (12a), 5'-O-(4,4-dimethoxytrityl)-2',3'-didehydro-2',3'-dideoxy-5-methyluridine (12b), 5'-O-acetyl-2',3'-didehydro-2',3'-dideoxyuridine and 5'-O-benzoyl-2',3'-didehydro-2',3'-dideoxyuridine (18b). To a stirred suspension NaBH$_4$ (12 mg) in anhydrous THF (5 mL), under argon, dimethyl ditelluride (50 µL, 0.3 mmol) was added, followed by several drops of dry ethanol until bubbles were formed. The suspension was heated to 50° C., then the THF solution or suspension (5 mL) of the starting material (anhydronucleosides: 8a, 8b, 17a, 17b or 17c, 3 mmol) was added. These reactions completed in 3-5 hours, which monitored by TLC. All solvents were evaporated under reduced pressure. The residues were then dissolved in $CH_2Cl_2$ and washed with water. Each $CH_2Cl_2$ solution was dried over MgSO$_4$ (s) and evaporated under reduced pressure. Each crude product was purified individually by silica gel column chromatography (gradient, 0-3% methanol in $CH_2Cl_2$) to give 69-90% yields of 12a, 12b, 18a or 18b (Table 1).

12a: $^1$H NMR (CDCl$_3$)$^{3d}$ δ: 3.47-3.48 (m, 2H), 3.82 (s, 6H), 4.97-4.98 (m, 1H), 5.06 (d, 1H, J=7.6 Hz), 5.89-5.91 (m, 1H), 6.35-6.37 (m, 1H), 6.84-6.86 (m, 4H), 7.05 (d, J=2.0 Hz, 1H), 7.27-7.38 (m, 9H), 7.85 (d, J=7.6 Hz, 1H); $^{13}$C NMR (CDCl$_3$) δ: 55.4, 64.2, 86.1, 86.9, 89.6, 102.2, 113.2, 127.1, 127.8, 127.4, 129.1, 130.20, 150.6, 127.1, 134.6, 141.4, 150.6, 158.6, 163.2; ESI-TOF: m/z calcd for $C_{30}H_{27}N_2O_6$ (M−H)$^-$ 512.1869, found 511.1861.

12b: $^1$H NMR (CDCl$_3$, identical to literature)$^{17}$ δ: 1.34 (s, 3H), 3.36-3.48 (m, 2H), 3.81 (s, 6H), 5.00 (m, 1H), 5.91-5.93 (m, 1H), 6.38-6.40 (m, 1H), 6.83-6.85 (m, 4H), 7.06 (m, 1H), 7.26-7.41 (m, 9H), 7.50 (s, 1H); $^{13}$C NMR (CDCl$_3$) δ: 14.1, 55.3, 64.6, 85.8, 86.4, 89.7, 111.8, 113.2, 127.1, 127.7, 127.4, 129.2, 130.2, 150.6, 133.1, 134.6, 141.4, 150.5, 158.7, 163.4; ESI-TOF: m/z calcd for $C_3$,H$_{29}$N$_2$O$_6$ (M−H)$^-$ 525.2026, found 525.2048.

18a: $^1$H NMR (CDCl$_3$, identical to literature)$^{7b}$ δ: 2.01 (s, 3H), 4.13-4.38 (m, 2H), 5.04 (m, 1H), 5.74 (d, J=7.6 Hz, 1H), 5.91 (m, 1H), 6.51 (m, 1H), 7.02 (m, 1H), 7.67 (d, J=8.6 Hz, 1H); ESI-TOF: m/z calcd for $C_{11}H_{11}N_2O_5$ (M−H)$^-$ 251.0668, found 251.0670.

18b: $^1$H NMR (DMSO-d$_6$, identical to literature)$^{18}$ δ: 4.43-4.51 (m, 2H), 5.15 (m, 1H), 5.18 (d, J=7.6 Hz, 1H), 6.02 (m, 1H), 6.51 (m, 1H), 6.89 (m, 1H), 7.25-7.85 (m, 5H), 7.92 (d, J=7.6 Hz, 1H). ESI-TOF: m/z calcd for $C_{16}H_{13}N_2O_5$ (M−H)$^-$ 313.0824, found 313.0825.

Example 7

Deprotection of protected 2',3'didehydro-2',3'-dideoxynucleosides.

This example describes the removal of the protecting groups to produce 1-(2,3-Dideoxy-β-D-glycero-pent-2-enofuranosyl)-uracil (19a, d4U) and 1-(2,3-Dideoxy-β-D-glycero-pent-2-enofuranosyl) thymine (2, d4T). From 12a and 12b: Activated Dowex 50 w (H$^+$ form, 100 mg) was added to a methanol solution (3 mL) of 12a or 12b (0.1 mmol), and the mixture was stirred for 10 minutes. The insoluble solid was filtered out and washed with methanol several times. The organic solution was evaporated to a small volume under reduced pressure and the residue was precipitated with pentane. The precipitate was collected by filtration and washed with ether to give pure d4U and d4T in 90% yield.

From 18a and 18b: Ammonia solution (conc., 0.5 mL) was added to a methanol solution (3 mL) of 18a or 18b (0.1 mmol). The reaction was stirred for an hour to complete the deprotection. The solvent was evaporated under reduced pressure. The crude product d4U or d4T was purified by silica gel column chromatography (gradient: 5-10% methanol in $CH_2Cl_2$) to offer a satisfied yield (80-90%).

19a (d4U): $^1$H NMR (DMSO-d$_6$, identical to literature)$^{10b}$ δ: 3.58-3.60 (m, 2H), 4.79-4.80 (m, 1H), 4.98 (m, 1H), 5.59 (d, J=8.0 Hz, 1H), 5.93-5.94 (m, 1H), 6.40-6.42 (m, 1H), 6.81 (m, 1H), 7.75 (d, J=8.0 Hz, 1H), 11.3 (m, 1H); ESI-TOF: m/z calcd for $C_9H_9N_2O_4$ (M−H)$^-$ 209.0562, found 209.0563.

2 (d4T): $^1$H NMR (DMSO-d$_6$, identical to literature)$^{7c}$ δ: 1.72 (s, 3H), 3.60-3.61 (m, 2H), 4.76-4.78 (m, 1H), 4.98 (br, 1H), 5.91-5.92 (m, 1H), 6.39-6.41 (m, 1H), 6.82 (m, 1H), 7.65 (s, 1H), 11.3 (m, 1H); ESI-TOF: $C_{10}H_{11}N_2O_4$, (M−H)$^-$ 223.0719, found 223.0721.

We claim:
1. A method of synthesizing 2',3'-didehydro-2',3'-dideoxynucleosides, the method comprising:
 (a) providing a 2,2'-anhydronucleoside;
 (b) contacting the 2,2'-anhydronucleoside with a nucleophile to form a product or an intermediate, wherein the nucleophile comprises a telluride dianion, or an alkyl or aryl telluride monoanion having from 1 to 24 carbon atoms; and
 (c) contacting the product or intermediate from step (b) with an oxidizing agent, a reducing agent, or a nucleophile to facilitate the elimination of a nucleophile-derived substituent, wherein the nucleophile-derived substituent comprises a telluride dianion-derived substituent, an alkyl or aryl telluride monoanion-derived substituent, or another leaving group from the product or the intermediate.

2. The method of claim 1, wherein the step of providing a 2,2'-anhydronucleoside comprises providing a 2,2'-anhydronucleoside having the following structure:

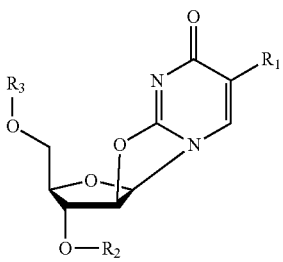

wherein $R_1$ is hydrogen or an alkyl having from 1 to 10 carbon atoms;
wherein $R_2$ is hydrogen or an electron withdrawing group; and
wherein $R_3$ is hydrogen or a protecting group.

3. The method of claim 1, wherein the step of providing a 2,2'-anhydronucleoside comprises providing a 2,2'-anhydronucleoside having the following structure:

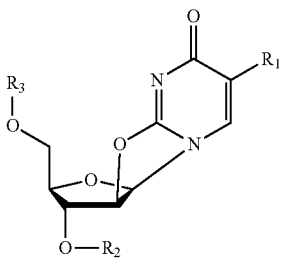

wherein $R_1$ is hydrogen or an alkyl having from 1 to 10 carbon atoms;
wherein $R_2$ is hydrogen, benzoyl, dimethoxytrityl (DMTr), trityl (Tr), alkyl (Ak) having from 1 to 12 carbon atoms, aryl (Ar) having up to 14 carbon atoms, benzyl (Bn), acetyl, methylbenzoyl, trifluoromethylbenzoyl, methanesulfonyl (Ms), trifluoromethanesulfonyl (Tf), para-toluenesulfonyl (Ts), chloro (Cl), bromo (Br), iodo (I), trimethylsilyl (TMS), tert-butyldimethylsilyl (TBDMS), an alternative trisubstituted silyl having from 3 to 24 carbon atoms, or an acyl having from 1 to 12 carbon atoms; and
wherein $R_3$ is hydrogen, benzoyl, dimethoxytrityl, trityl (Tr), alkyl (Ak) having from 1 to 12 carbon atoms, aryl (Ar) having up to 14 carbon atoms, benzyl (Bn), methylbenzoyl, trifluoromethylbenzoyl, trimethylsilyl (TMS), tert-butyldimethylsilyl (TBDMS), acetyl, an acyl having from 1 to 12 carbon atoms, or an alternative trisubstituted silyl having from 3 to 24 carbon atoms.

4. The method of claim 1, wherein each of the alkyl or aryl telluride monoanion comprises a methyl telluride monoanion or a phenyl telluride monoanion.

5. The method of claim 1, wherein the method further comprises a step of generating the alkyl or aryl telluride monoanion, and wherein the step of generating includes a step of reducing a ditelluride reagent having the formula:

$$R_1Te\text{-}TeR_2$$

wherein $R_1$ and $R_2$ each consist of an alkyl or an aryl group having from 1 to 24 carbon atoms.

6. The method of claim 5, wherein the step of reducing a ditelluride reagent includes reducing the ditelluride reagent by contacting with sodium borohydride, $LiAlH_4$, $LiBH_4$, $B_2H_6$, NaHS, $NaHSO_3$, Zn, Fe, Al, or $H_2$.

7. The method of claim 1, wherein the oxidizing agent comprises iodine/water, air, $O_2$, $NaIO_4$, or $H_2O_2$.

8. The method of claim 1, wherein the reducing reagent comprises sodium borohydride, $LiAlH_4$, $LiBH_4$, $B_2H_6$, NaHS, $NaHSO_3$, Zn, Fe, Al, or $H_2$.

9. The method of claim 1, wherein the 2,2'-anhydronucleoside has an α-2'-position, and wherein the step of contacting the 2,2'-anhydronucleoside with a nucleophile comprises a step of reacting the nucleophile at the α-2'-position of the 2,2'-anhydronucleoside.

10. The method of claim 1, wherein the 2,2'-anhydronucleoside has a 1'-2' bond, and wherein the method further comprises a step of eliminating the nucleophile-derived substituent across the 1'-2' bond of the 2,2'-anhydronucleoside.

11. The method of claim 1, wherein the 2,2'-anhydronucleoside has a 2'-3' bond, and wherein the method further comprises a step of eliminating the nucleophile-derived substituent across the 2'-3' bond of the 2,2'-anhydronucleoside.

12. A compound having the formula:

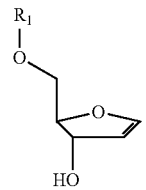

wherein $R_1$ is dimethoxytrityl, trityl (Tr), alkyl (Ak) having from 1 to 12 carbon atoms, aryl (Ar) having up to 14 carbon atoms, benzyl (Bn), benzoyl, methylbenzoyl, trifluoromethylbenzoyl, trimethylsilyl (TMS), tert-butyldimethylsilyl (TBDMS), acetyl, an acyl having from 1 to 12 carbon atoms, or an alternative trisubstituted silyl having from 3 to 24 carbon atoms.

* * * * *